United States Patent
Nauche et al.

(10) Patent No.: US 9,980,639 B2
(45) Date of Patent: May 29, 2018

(54) VISUAL COMPENSATION SYSTEM AND OPTOMETRIC BINOCULAR DEVICE

(71) Applicant: ESSILOR INTERNATIONAL (COMPAGNIE GENERALE D'OPTIQUE), Charenton-le-Pont (FR)

(72) Inventors: Michel Nauche, Charenton-le-Pont (FR); Stephane Boutinon, Charenton-le-Pont (FR)

(73) Assignee: ESSILOR INTERNATIONAL (COMPAGNIE GENERALE D'OPTIQUE), Charenton-Le-Pont (FR)

(*) Notice: Subject to any disclaimer, the term of this patent is extended or adjusted under 35 U.S.C. 154(b) by 0 days. days.

(21) Appl. No.: 15/112,538

(22) PCT Filed: Jan. 15, 2015

(86) PCT No.: PCT/FR2015/050103
§ 371 (c)(1),
(2) Date: Jul. 19, 2016

(87) PCT Pub. No.: WO2015/107303
PCT Pub. Date: Jul. 23, 2015

(65) Prior Publication Data
US 2016/0331226 A1    Nov. 17, 2016

(30) Foreign Application Priority Data
Jan. 20, 2014    (FR) ...................... 14 50433

(51) Int. Cl.
*A61B 3/02*    (2006.01)
*A61B 3/028*    (2006.01)
(Continued)

(52) U.S. Cl.
CPC .............. *A61B 3/0285* (2013.01); *A61B 3/036* (2013.01); *G02B 3/14* (2013.01); *G02B 7/023* (2013.01)

(58) Field of Classification Search
CPC ......... A61B 3/0285; A61B 3/036; A61B 3/04; A61B 3/028; A61B 3/08; A61B 3/1035; G02C 2202/22; G02C 7/083; G02C 7/101
(Continued)

(56) References Cited

U.S. PATENT DOCUMENTS 5,648,833 A * 7/1997 Doms .................. A61B 3/0285
351/233
2004/0032568 A1    2/2004 Fukuma et al.
(Continued)

FOREIGN PATENT DOCUMENTS

EP    1 676 523 A1    7/2006
EP    2 034 338 A1    3/2009

OTHER PUBLICATIONS

International Search Report, dated Apr. 15, 2015, from corresponding PCT Application.

*Primary Examiner* — Mahidere Sahle
(74) *Attorney, Agent, or Firm* — Young & Thompson

(57) ABSTRACT

A visual compensation system (10) enabling observation, with variable optical power correction, along an optical observation axis (X) includes:—a first rotatable optical element (2) centered on the optical axis (X) and having a first cylinder power along the optical axis (X); —a second rotatable optical element (4) centered on the optical axis (X) and having a second cylinder power along the optical axis (X); and—a lens (6) having the optical axis (X) as the axis thereof, and moreover having variable sphere power.

23 Claims, 2 Drawing Sheets

(51) Int. Cl.
*A61B 3/036* (2006.01)
*G02B 3/14* (2006.01)
*G02B 7/02* (2006.01)

(58) Field of Classification Search
USPC .................................................. 351/233–236
See application file for complete search history.

(56) References Cited

U.S. PATENT DOCUMENTS

2009/0153796 A1  6/2009 Rabner
2013/0222710 A1* 8/2013 Huh ....................... A61F 9/022
                                                    349/14

\* cited by examiner

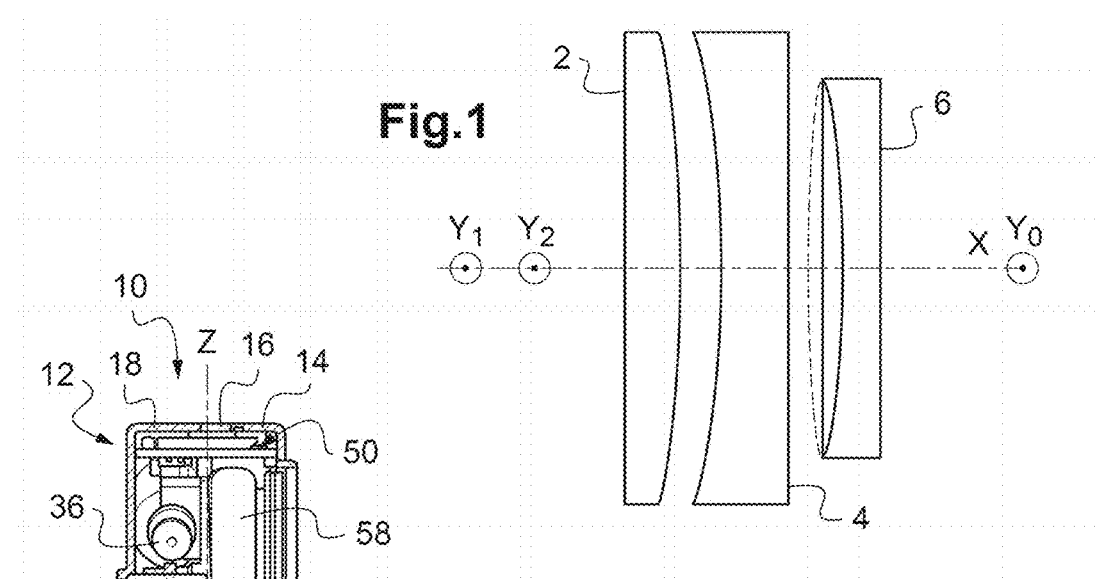
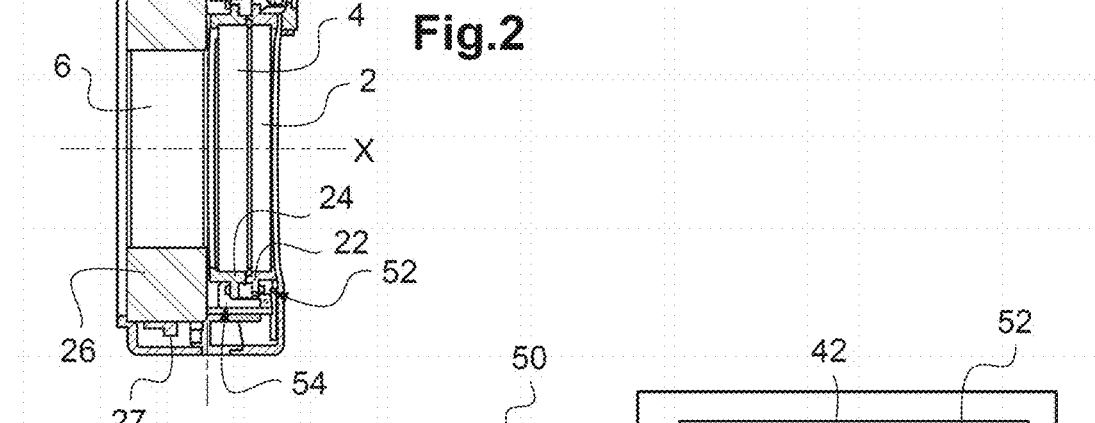
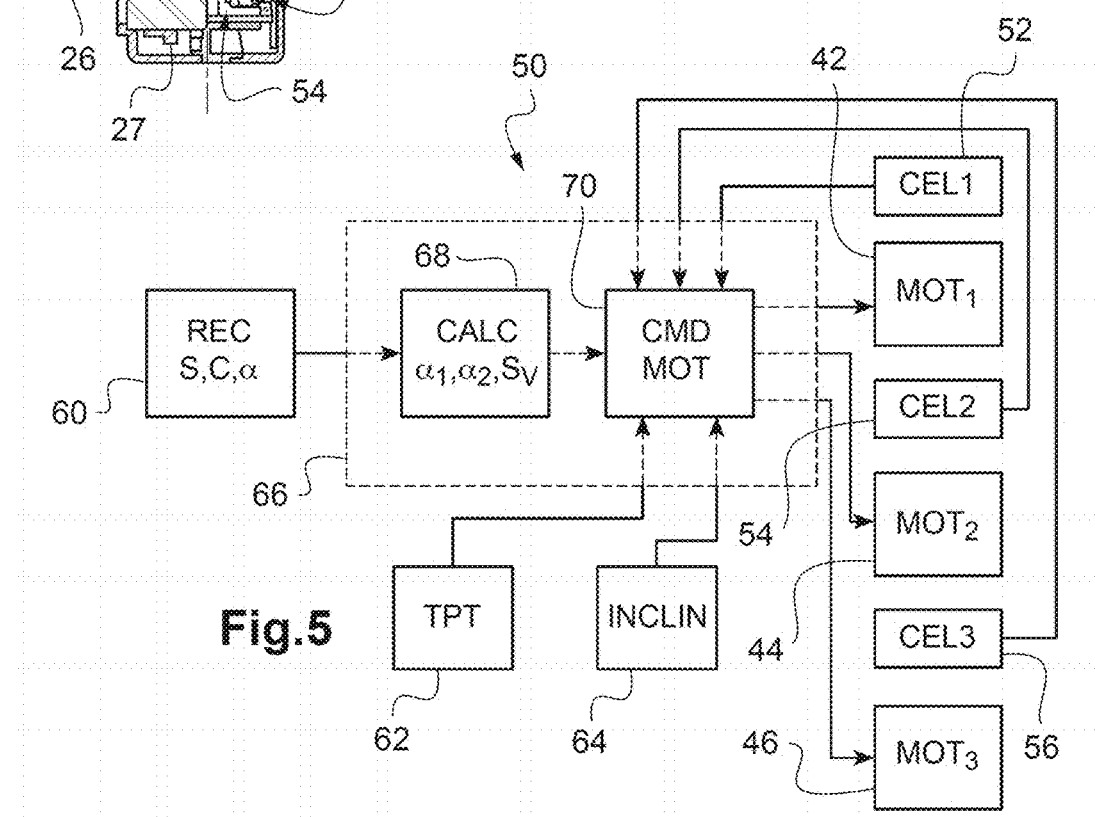

VISUAL COMPENSATION SYSTEM AND OPTOMETRIC BINOCULAR DEVICE

TECHNICAL FIELD TO WHICH THE INVENTION RELATES

The present invention generally relates to the field of optometry.

It more particularly relates to a visual compensation system and to an optometric binocular device comprising such a system.

TECHNOLOGICAL BACKGROUND

In the context of the measurement of the visual acuity of a patient, it has already been proposed to simulate the visual compensation to be provided, for example by means of trial frames or a refractor such as a phoropter.

Trial frames are able to receive, in succession, trial lenses providing different corrections, until the suitable correction for the patient is found.

This solution is impractical and requires trial lenses to be stored separately in dedicated boxes. It furthermore involves lens changes, resulting in undesired and non-continuous transitions in corrective power.

In phoropters, trial lenses are placed on a plurality of disks that are rotated manually or using a motorized mechanism.

However, it will be understood that such an object has a substantial bulk and weight related to the number of lenses placed on each disk.

In addition, the field of view through the phoropter is limited (tunnel effect) because of the plurality of lenses that are aligned in order to obtain various correctional values.

Before presenting the invention, a few definitions of notions used in the following description will be recalled.

Optical power is the degree to which an optical element is able to make light rays converge or diverge. It is expressed in diopters and corresponds to the inverse of focal length in meters.

Spherical power is spoken of when the optical power is the same in all the meridian planes of the lens (rotational symmetry about the optical axis).

In contrast, astigmatism is spoken of when the optical power varies depending on the meridian of the lens. In the case of an astigmatic optical element, cylindrical power is spoken of i.e. the difference between the maximum optical power along a first meridian and the minimum optical power along a second meridian. This is the case of toric or cylindrical surfaces.

SUBJECT OF THE INVENTION

In this context, the present invention provides a visual compensation system allowing observation along an optical axis of observation with an optical correction of variable power, characterized in that it comprises a first optical element rotatable with a rotary movement centered on the optical axis and having a first cylindrical power along the optical axis, a second optical element rotatable with a rotary movement centered on the optical axis and having a second cylindrical power along the optical axis, and a lens having for axis said optical axis and of variable spherical power.

The first optical element and the second optical element may be independently rotatable one from the other so that, in at least one position, the resultant cylindrical power generated by the combination of the first optical element and the second optical element has a negligible value, for example lower than 0.1 diopters, or even a value of zero.

In practice, the absolute value of the second cylindrical power is for example equal (or at least almost equal) to the absolute value of the first cylindrical power, so that said resultant cylindrical power value is zero (or almost zero) in at least one position.

In other words, in this case, the second cylindrical power is equal or opposite to the first cylindrical power. The first electrical power and the second cylindrical power may however be different in order to compensate for the spacing between the two lenses (according to Gullstrand's equation) so as to obtain an alignment the combined (i.e. resultant) cylindrical power of which cancels out in at least one position.

Thus, by varying the angular position of the first optical element (angle $\alpha_1$ in the description that follows) and the angular position of the second optical element (angle $\alpha_2$ in the description that follows), independently one from the other, and the spherical power $S_V$ of the lens of variable spherical power, it is possible to independently vary the spherical power S, the cylindrical power C and the angle of astigmatism $\alpha$ of the system (formed by the first optical element, the second optical element and the lens of variable spherical power) over predefined ranges, as explained in the description that follows.

In particular, by virtue of the ability to vary the relative orientation of the two optical elements of cylindrical power, there is at least one position of the system in which the cylindrical power C of the system is low. When the first cylindrical power and the second cylindrical power are equal or almost equal in absolute value, there is at least one relative position of these two elements in which the cylindrical power C of the system is negligible or even zero. It is thus possible to generate a correction of solely spherical power.

Moreover, it will be noted that the variable spherical power especially makes it possible to compensate for the spherical power created by the association of the optical elements of cylindrical power, either in order to cancel it out, or in order to obtain in total (for the complete system) a spherical power in accordance with the desired spherical power. Thus, the spherical power induced by the combination of the first optical element and the second optical element may be at least in part compensated for by the lens of variable spherical power.

This visual compensation system is thus particularly suitable for generating variable corrections; in addition it has a low bulk because three optical elements are enough to produce variable corrections in the aforementioned ranges of parameters.

This system furthermore allows the Jackson-cross-cylinder function to be provided by rapid rotation of the two optical elements of cylindrical power. To provide this function (frequently used in refraction protocols), a crossed bicylinder composed of two plane-cylindrical lenses of perpendicular axes and of opposite signs and identical powers are used. Its spherical power is zero, it is used to very rapidly vary the value of the cylindrical power by rotating the bicylinder. This rapid variation is achievable here without addition of supplementary optical elements, by driving the first optical element and the second optical element to rotate in concert.

The lens of variable spherical power is for example a deformable lens containing a fluid, or, in other words, a lens containing a fluid and a deformable membrane.

Provision may be made for a first mechanism driven by a first motor and designed to rotate the first optical element with a rotary movement centered on the optical axis and optionally for a second mechanism driven by a second motor and designed to rotate the second optical element with a rotary movement centered on the optical axis.

The first mechanism and the first motor on the one hand and the second mechanism and the second motor on the other hand form a first actuator and a second actuator, respectively, each allowing the position of one of the first and second optical elements to be adjusted.

The visual compensation system may comprise a control element designed to respectively control the first motor and the second motor depending on setpoint data, for example setpoint data received from a remote control manipulated by a user of the system.

The control element for example comprises a temperature sensor and/or a sensor of orientation or of movement designed to deliver an orientation datum.

Provision may especially be made for the control element to comprise a computing machine designed to generate control signals depending on at least one of said setpoint data and said orientation datum and to emit control signals respectively addressed to the first motor and to the second motor.

The control signals sent to the motor will thus take into account the orientation of the visual compensation system, for example in order to compensate for power effects induced in the liquid lens due to gravity.

The control element may also be designed to generate control signals depending on at least one of said setpoint data and a distance between a portion of the system and an eye observing through the system.

The first mechanism may comprise a first cog that interacts for example with a first worm screw that is securely fastened to a driveshaft of the first motor; the first optical element may then be mounted on the first cog.

Likewise, the second mechanism may comprise a second cog that interacts for example with a second worm screw that is securely fastened to a driveshaft of the second motor; the second optical element may then be mounted on the second cog.

Such mechanisms allow the output speed of the motor to be decreased. The visual compensation system thus has a particularly fine resolution and the parameters S, C and α, that define the correction of the system may thus have an almost continuous set of values in the aforementioned ranges. In addition, by virtue of such mechanisms, the cogs, and therefore the optical elements borne by these cogs, are maintained in position even in the absence of a power supply to the motors. The optical elements (i.e. the first optical element, the second optical element and the lens) are thus mounted (in the visual compensation system) so that they (each) preserve their respective setpoint positions (even) without supply of electrical power.

The visual compensation system may comprise at least one optical cell associated with said cogs (in practice one optical cell associated with each cog) so as to determine the position of the associated optical element (either the first optical element, the second optical element or the lens).

The visual compensation system may be housed in a casing for example formed by assembling at least one first portion and one second portion; it is possible to make provision for the first cog to be rotatably mounted on said first portion and for the second cog to be rotatably mounted on said second portion.

The first motor is for example mounted on said first portion and/or the second motor is for example mounted on said second portion.

Provision may also be made for a third mechanism driven by a third motor to be designed to drive a ring for controlling the spherical power of the lens of variable spherical power to rotate.

The spherical power may thus also be adjusted by means of an actuator formed from the third motor and the third mechanism.

The third mechanism for example comprises a first cog that interacts with a third worm screw that is securely fastened to a driveshaft of the third motor, the controlling ring being securely fastened to the third cog.

The first motor, the second motor and the third motor are for example placed so as to free a circular geometry over at least 120°, for example over 180°, said geometry being centered on the optical axis as close as possible to the effective radius of the lenses, for example at a distance smaller than 20 mm (or even smaller than 10 mm) from the effective radius of the lenses; thus an assembly of low bulk is obtained.

The aforementioned control element (for example by means of its aforementioned computing machine) may be designed to generate at least one control signal, addressed to the third motor, depending on at least one of said setpoints and on a temperature datum generated by the temperature sensor. It is thus possible to compensate for variations in the spherical power of the lens of variable spherical power due to any variations in temperature.

The casing may moreover comprise a third portion, the third motor possibly then being mounted in the third portion.

According to envisionable embodiments (for example that described below), the first optical element is a first diopter formed on a face of a first planar-cylindrical lens and/or the second optical element is a second diopter formed on a face of a second planar-cylindrical lens. Precisely, provision may be made for the first lens to be a convex planar-cylindrical lens and/or for the second lens to be a concave planar-cylindrical lens.

Moreover, the first optical element, the second optical element and the lens may be controlled so as to provide a Jackson-cross-cylinder function i.e. so that the cylindrical power and/or angle of astigmatism of the system formed from the first optical element, the second optical element and the lens (each) alternate between two distinct values.

In other words, the invention provides a visual compensation system allowing observation along an optical axis of observation with an optical correction of variable power, characterized in that it comprises:
   a first optical element rotatable with a rotary movement centered on the optical axis and having a first cylindrical power along the optical axis;
   a second optical element rotatable with a rotary movement centered on the optical axis and having a second cylindrical power along the optical axis;
   a lens having for axis said optical axis, of variable spherical power and mechanically actuatable so as to make said spherical power vary continuously.

The invention also provides an optometric binocular device comprising two optical systems, which are for example mounted on a common holder, in which one of the two optical systems (or even each of the two optical systems) is a visual compensation system as presented above.

DETAILED DESCRIPTION OF ONE EXEMPLARY EMBODIMENT

The description which follows with regard to the appended drawings given by way of nonlimiting examples will clearly elucidate the essence of the invention and the manner in which it may be carried out.

In the appended drawings:

FIG. 1 schematically shows the optical elements used in one exemplary implementation of the invention;

FIG. 2 shows a cross-sectional view of an exemplary visual compensation system according to the teachings of the invention;

Figure 3:
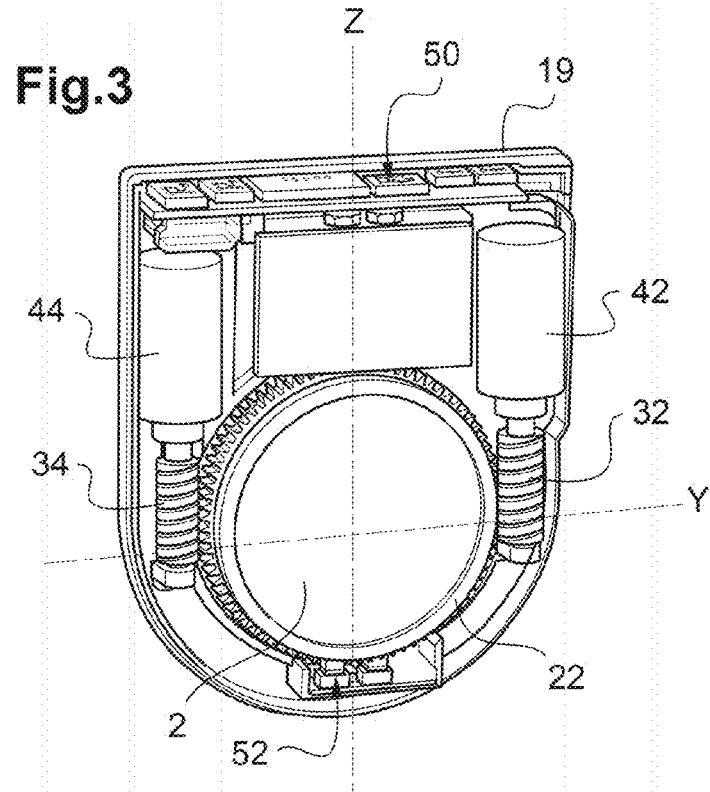
FIG. 3 shows a cutaway view of the visual compensation system in FIG. 2, from the side of the cylindrical lenses.

FIG. 5 schematically shows an element for controlling the visual compensation system in FIG. 2.

FIG. 1 schematically shows the main optical elements of an exemplary visual compensation system according to the teachings of the invention.

These optical elements comprise a convex planar-cylindrical lens 2, of cylindrical power $C_0$, a concave planar-cylindrical lens 4, of negative cylindrical power $-C_0$, and a lens 6 of variable spherical power $S_V$.

The absolute value (or modulus), here $C_0$, of the cylindrical power (here $-C_0$) of the concave planar-cylindrical lens 4 is therefore equal to the absolute value ($C_0$) (or modulus) of the cylindrical power ($C_0$) of the convex planar-cylindrical lens 2.

The three lenses 2, 4, 6 are placed on the same optical axis X. Precisely, each of the three lenses 2, 4, 6 has a generally cylindrical exterior shape centered on the optical axis X. In the example described here, the lenses 2, 4, 6 have the following diameters (quantifying their bulk), respectively: 25 mm, 25 mm, 20 mm.

It will be noted that it is preferable to use this visual compensation system 10 with the eye of the patient located on the side of the variable spherical power lens 6 so that the lenses 2, 4 of cylindrical power, which are larger in diameter, do not limit the field of view defined by the variable spherical power lens 6, which itself is perceived as wide due to its proximity to the eye of the patient.

Each of the three lenses 2, 4, 6 comprises a first planar face, perpendicular to the optical axis X, and a second face, opposite the first face and optically active:

the optically active face of the lens 2 is cylindrically convex in shape (the axis $Y_1$ of the cylinder defining this face lying perpendicular to the optical axis X);

the optically active face of the lens 4 is cylindrically concave in shape (the axis $Y_2$ of the cylinder defining this face lying perpendicular to the optical axis X); and the optically active face of the lens 6 of variable spherical power $S_V$ is deformable and may thus adopt a convex spherical shape (as illustrated by the dotted line in FIG. 1), a planar shape or a concave spherical shape (as illustrated by the solid line).

The lens 6 of variable spherical power $S_V$ is for example a lens of the type described in document EP 2 034 338. Such a lens comprises a cavity closed by a transparent deformable membrane and a planar movable transparent wall; the cavity contains a transparent liquid of constant volume that is constrained, to a greater or lesser degree, by the movable face, in order to deform the membrane that is thus either a spherical concave surface, or a planar surface, or a spherical convex surface. In the lens used, a transformation of motion made up of a nut/bolt system ensures transformation of rotary and linear motion. Thus, rotating a ring mounted on a casing 26 translates a part of the lens 6, thereby causing the aforementioned deformation of the transparent membrane, as explained for example in the aforementioned document EP 2 034 338. It is thus possible to vary the spherical power $S_V$ continuously via mechanical action on the lens 6. In the example described here, the lens 6 has a variable focal length of between −40 mm and 40 mm, i.e. a variable spherical power $S_V$ of between −25D and 25D (D being the diopter, the unit for measuring vergence, inverse to focal length expressed in meters).

Moreover, the planar-cylindrical lenses 2, 4 have respectively as already indicated a cylindrical power of $-C_0$ and $C_0$, here with $C_0$=5D.

As explained in greater detail below, the concave planar-cylindrical lens 4 and the convex planar-cylindrical lens 2 are rotatably mounted about the axis X (rotary movement centered on the axis X).

The axis $Y_1$ of the convex cylinder formed on the optically active face of the convex planar-cylindrical lens 2 may thus make a variable angle $\alpha_1$ with a reference axis $Y_0$ (which is fixed and perpendicular to the optical axis X).

Likewise, the axis $Y_2$ of the concave cylinder formed on the optically active face of the concave planar-cylindrical lens 4 may make a variable angle $\alpha_2$ with the reference axis $Y_0$.

By calculating the vergence on the various meridians, the following formulae are obtained for the spherical power S, the cylindrical power C and the angle of astigmatism $\alpha$ of the system formed from the three optical elements 2, 4, 6 just described:

$$\tan 2\alpha = \frac{\sin 2\alpha_2 - \sin 2\alpha_1}{\cos 2\alpha_2 - \cos 2\alpha_1} = -\frac{\cos(\alpha_1 + \alpha_2)}{\sin(\alpha_1 + \alpha_2)} \quad \text{(formula 1)}$$

$$C = C_0(\cos 2(\alpha - \alpha_2) - \cos 2(\alpha - \alpha_1)) \quad \text{(formula 2)}$$

$$S = S_V - \frac{C}{2}. \quad \text{(formula 3)}$$

It will be noted that the term ($-C/2$) in formula 3 corresponds to spherical power generated by the resultant of the 2 lenses providing cylindrical power.

By controlling the rotational position of the convex planar-cylindrical lens 2 and the rotational position of the concave planar-cylindrical lens 4, independently of one another, as described hereinafter, it is possible to independently vary each of the angles $\alpha_1$, $\alpha_2$ from 0° to 360° and thus obtain an adjustable cylindrical power C of between −2.0 and 2.0 (i.e. here between −10D and 10D), and for any angle of astigmatism adjustable between 0° and 360° obtained by simultaneous control of the two lenses. As formula 3 indicates, the spherical power resulting from the resultant of the orientation of the 2 cylindrical lenses is compensated for using the lens of variable spherical power.

Moreover, by varying the spherical power $S_V$ of the spherical lens 6, it is possible to adjust the spherical power S of the system formed from the three lenses 2, 4, 6.

According to one envisionable variant, the lenses providing a set cylindrical power could have the same (positive or negative) cylindrical power $C_0$: it could be a question of two, optionally identical, convex planar-cylindrical lenses or, as an alternative, of two, optionally identical, concave planar-cylindrical lenses.

Specifically, in this case, the spherical power S, the cylindrical power C and the angle of astigmatism $\alpha$ of the system formed from these two lenses and from a lens providing variable spherical power are given by the following formulae:

$$\tan 2\alpha = \frac{\sin 2\alpha_2 + \sin 2\alpha_1}{\cos 2\alpha_2 + \cos 2\alpha_1} \quad \text{(formula 4)}$$

$$C = C_0(\cos 2(\alpha - \alpha_2) + \cos 2(\alpha - \alpha_1)) \quad \text{(formula 5)}$$

$$S = S_V + C_0 - \frac{C}{2}. \quad \text{(formula 6)}$$

The term $C_0-C/2$ corresponds to the spherical power induced by the combination of the two lenses providing cylindrical power.

It is therefore also possible in this case to adjust the spherical power S, the cylindrical power C and the angle of astigmatism α, in particular so that the cylindrical power C is zero, by rotating the lenses providing cylindrical power (independently of each other) and by varying the spherical power of the lens providing variable spherical power.

An exemplary visual compensation system 10 that uses the optical elements that have just been described is shown in FIG. 2.

Sometimes in the following description, in order to clarify the explanation, terms such as "upper" or "lower" will be used, which define an orientation in FIGS. 2, 3 and 4. It will be understood that this orientation is not necessarily applicable to the use that will possibly be made of the system described, in which use the only reference direction is the optical axis X.

The visual compensation system 10 comprises a casing 12 formed from a first portion 14, a second portion 16 and a third portion 18, which are placed in succession along the optical axis X and assembled pairwise in planes perpendicular to the optical axis X.

A first cog 22 is mounted so as to be able to rotate with a rotary movement centered on the optical axis X in the first portion 14 of the casing 12 and bears, at its center, in an aperture provided for this purpose, the convex planar-cylindrical lens 2. The first cog 22 and the convex planar-cylindrical lens 2 are coaxial; in other words, in cross section in a plane perpendicular to the optical axis X, the exterior circumference of the first cog 22 and the circumference of the convex planar-cylindrical lens 2 form concentric circles centered on the optical axis X.

Likewise, a second cog 24 is mounted so as to be able to rotate with a rotary movement centered on the optical axis X in the second portion 16 of the casing 12 and bears, at its center, in an aperture provided for this purpose, the concave planar-cylindrical lens 4. The second cog 24 and the concave planar-cylindrical lens 4 are coaxial; in other words, in cross section in a plane perpendicular to the optical axis X, the exterior circumference of the second cog 24 and the circumference of the concave planar-cylindrical lens 4 form concentric circles centered on the optical axis X.

A third cog 27 is mounted so as to be able to rotate with a rotary movement centered on the optical axis X in the third portion 18 of the casing 12. The third cog 27 is securely fastened to the ring provided on the circumference of the casing 26 that bears the lens 6 of variable spherical power and allowing the spherical power $S_V$ to be controlled. The casing 26 of the lens 6 of variable spherical power is mounted in the third portion 18 of the casing 12.

As may be clearly seen in FIG. 3, the first cog 22 is rotated (about the optical axis X) by means of a first motor 42 a driveshaft of which bears a first worm screw 32 that engages with the first cog 22. The first motor 42 is for example mounted in the first portion 14 of the casing 12.

The current position of the first cog 22 is monitored by a first optical cell 52.

Likewise, the second cog 24 is rotated about the optical axis X by means of a second motor 44 a driveshaft of which bears a second worm screw 34 that engages with the second cog 24. The second motor 44 is for example mounted in the second portion 16 of the casing 12.

The current position of the second cog 24 is monitored by a second optical cell 54.

Figure 4:
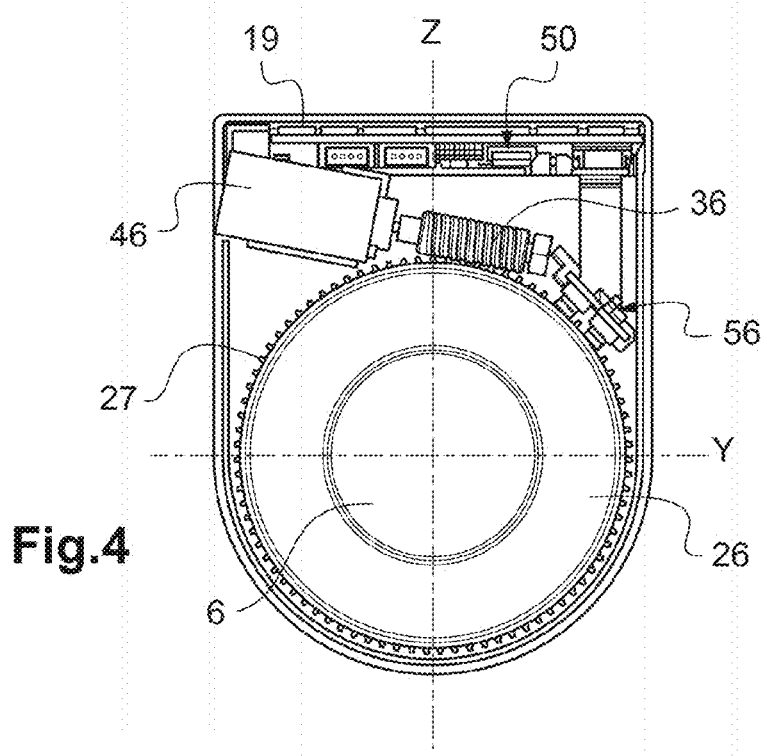
FIG. 4 shows a cutaway view of the visual compensation system in FIG. 2, from the side of the variable spherical lens.

As shown in FIG. 4, the third cog 27 is for its part rotated (about the optical axis X) by means of a third motor 46 that has a driveshaft on which a third worm screw 36 that engages with the third cog 27 is mounted. The third motor 46 is for example mounted in the third portion 18 of the casing 12.

The current position of the third cog 27 is monitored by a third optical cell 56.

Each optical cell 52, 54, 56 is for example formed from a couple of elements comprising at least one optical sensor; the other element of the pair is for example an optical emitter (or, as a variant, a reflective element, in which case an optical emitter is associated with the optical sensor).

The first, second and third motors 42, 44, 46 are for example stepper motors having a resolution of 20 steps/turn, here set in 8ths of a step (referred to as micro-steps below). As a variant, these motors could be set in 16ths of a step.

The internal volume of the casing 12 (and moreover the internal volume of each of the first, second and third portions 14, 16, 18 in the same way) may be subdivided into a space for receiving the motors 42, 44, 46 (upper region of the casing 12 in FIGS. 2, 3 and 4) and a space for receiving the optical elements 2, 4, 6 (lower region of the casing 12 in FIGS. 2, 3 and 4).

The space for receiving the motors 42, 44, 46 has an essentially parallelepipedal shape open (toward the bottom in the figures) in the direction of the space for receiving the optical elements 2, 4, 6 and closed at the opposite end (toward the top in the figures) by an upper face 19 of the casing 12 (the upper face 19 of the casing 12 being formed by the assembled upper faces of the first, second and third portions 14, 16, 18 of the casing 12, respectively).

The arrangement of the motors 42, 44 and 46 is such as to advantageously make it possible to use a circular geometry over 180°, said circular geometry being centered on the optical axis as close as possible to the effective radius of the lenses.

The space for receiving the optical elements 2, 4, 6 has, in contrast to the space for receiving the motors, a cylindrical shape (bounded by the walls of the casing 12) that matches that of the third cog 27 over half the circumference of the latter.

In other words, the casing 12 (and therefore each of the first, second and third portions 14, 16, 18 of the casing 12) has, in the space for receiving the optical elements 2, 4, 6, a cylindrical shape with a diameter (perpendicular to the optical axis X) that is about the same as, and slightly larger than, that of the third cog 27.

The respective diameters of the cogs 22, 24, 27 are chosen so as to preserve the field despite the thickness of the optical system.

The first motor 42 and the first worm screw 32 extend in the casing 12 in a direction Z perpendicular to the upper face of the casing 12 (and therefore especially perpendicular to the optical axis X) in such a way that the first motor 42 is housed in the space for receiving the motors whereas the first worm screw 32 lies in the space for receiving the optical elements.

As for the second motor 44 and the second worm screw 34, they extend in the casing 12 in the same direction, but opposite the first motor 42 and the first worm screw 34 relative to the cylindrical power lenses 2, 4. The second motor 44 is housed in the space for receiving the motors whereas the second worm screw 34 lies in the space for receiving the optical elements.

Thus, it will be noted that the first worm screw 32 and the second worm screw 34 are located on either side of the assembly formed by the first cog 22 and the second cog 24, and that the lateral bulk (along an axis Y perpendicular to the aforementioned axes X and Z) of these various parts (first worm screw 32, second worm screw 34, first or second cog 22, 24) is smaller than the diameter of the third cog 27 so that the first and second worm screws 32, 34 are contained in the space for receiving the optical elements without extra room being required to receive them.

Moreover, the first and second motors 42, 44 each have a bulk along the optical axis X larger than that of each of the first and second cogs 22, 24, and even larger than that of each of the first and second portions 14, 16 of the casing 12. However, because these first and second motors 42, 44 are placed as indicated above on each side of the casing 12 (relative to the axis Z), they may each occupy a space that extends, along the optical axis X, in line with the first portion 14 and the second portion 16 of the casing 12.

For example, each of the first and second motors 42, 44 has a lateral bulk (outside diameter of the motor) comprised between 6 and 12, for example 10 mm, whereas the first and second cogs 22, 24 each have a thickness (bulk along the axis X) comprised between 1 and 4, for example 2.5 mm.

The third motor 46 and the third worm screw 36 are in contrast located in the space for receiving the motors, in the region that extends along the axis X in line with the third portion 18 of the casing 12. Thus, the third worm screw 36 engages with the third cog 27 in an upper portion of the latter, thereby making it possible for the casing 12 to follow closely the shape of the casing 12 in the lower portion of the third cog 27, as indicated above.

In the example described, as shown in FIG. 4, the axis of the third motor 46 and the third worm screw 36 is slightly inclined relative to the upper face of the casing 12 (specifically relative to the aforementioned axis Y).

Provision may for example be made for the thickness of the third cog 27 to be comprised between 0.3 mm and 2 mm.

This arrangement of the various elements allows a relatively thin casing to be obtained, typically having a thickness comprised between 15 and 20 mm.

The casing 12 also comprises, for example in the upper region of the space for receiving the motors, a control element 50, here formed of a plurality of integrated circuits borne by a common printed circuit board.

Moreover a device for storing electrical power, here a battery 58 (though, as a variant, it could be a supercapacitor), is provided in order to make the apparatus standalone. Provision may for example also be made for contactless elements for recharging the power storing device 58. The battery 58 especially allows the motors 42, 44, 46 and the control element 50 to be supplied with electrical power.

The main elements of such a control element 50, and their connections to the aforementioned motors 42, 44, 46 and to the aforementioned optical cells 52, 54, 56, are schematically shown in FIG. 5.

The control element 50 comprises a receiving module 60 designed to receive, here via a wireless link, setpoint data, i.e. data indicating the values desired by the user for the spherical power S, the cylindrical power C and the angle of astigmatism α that define the compensation generated by the optical system formed from the optical elements 2, 4, 6.

The receiving module 60 is for example an infrared receiving module that receives this setpoint data from an infrared emitting remote control controlled by the user. As a variant, provision could be made for these setpoint data to be received from a personal computer via a wireless link, for example a local wireless network; the user could in this case choose values of spherical power S, cylindrical power C and angle of astigmatism α for the visual compensation system by interactive selection on the computer.

The receiving module 60 transmits the setpoint data S, C, α received to a computing machine 66 (for example consisting of a processor executing a computer program so as to perform the functions of the computing machine, as described below), specifically to a computational module 68 controlled by this computing machine 66.

The computational module 68 computes the values of the angles $\alpha_1$, $\alpha_2$ and the value of spherical power $S_V$ required in order to obtain the setpoint values S, C, α received as input, using the formulae given above. In the case where the planar-cylindrical lenses 2 and 4 have a cylindrical power of $-C_0$ and $C_0$, respectively, the following formulae will for example be used:

$$\begin{cases} \alpha_1 = \alpha - \frac{1}{2}\arcsin\left(\frac{C}{2C_0}\right) + \frac{\pi}{4} \\ \alpha_2 = \alpha + \frac{1}{2}\arcsin\left(\frac{C}{2C_0}\right) + \frac{\pi}{4} \end{cases}$$

$$S_V = S + \frac{C}{2}$$

The computing machine 66 also comprises a control module 70 that receives as input the values of angles $\alpha_1$, $\alpha_2$ and spherical power $S_V$ computed by the computational module 68 and emits control signals to the motors 42, 44, 46, in order to control each of the motors 42, 44, 46 independently of the others and obtain respective positions for the cogs 22, 24, 27 that allow the desired values to be obtained:

the control module 70 controls the first motor 42 so as to make the first cog 22 turn about the optical axis X as far as the position in which the axis $Y_1$ of the optically active cylindrical surface of the convex planar-cylindrical lens 2 (borne by the first cog 22) makes an angle $\alpha_1$ with the reference direction $Y_0$;

the control module 70 controls the second motor 44 so as to make the second cog 24 turn about the optical axis X as far as the position in which the axis $Y_2$ of the optically active cylindrical surface of the concave planar-cylindrical lens 4 (borne by the second cog 24) makes an angle $\alpha_2$ with the reference direction $Y_0$; and the control module 70 controls the third motor 46 so as to make the third cog 27 turn about the optical axis X as far as the position in which the control ring of the variable spherical power sets the spherical power $S_V$ to the power computed by the computational module 68.

The position of each cog 22, 24, 27 is known at each instant by virtue of the optical cells 52, 54, 56, respectively, which each measure, on the cog with which each is associated, the number of teeth that have passed through the optical cell relative to a reference point on the circumference of the wheel in question (for example a point devoid of teeth).

In the example described here, the first motor 42/first worm screw 32/first cog 22 assembly, just like the second motor 44/second worm screw 34/second cog 24 assembly, has a gear ratio such that one turn of the cog 22, 24 corresponds to 15040 micro-steps of the associated motor 42, 44. The resolution (angle of rotation of the cogs 22, 24 for one micro-step) is therefore 0.024° for the angles $\alpha_1$ and $\alpha_2$.

The third motor 46/third worm screw 36/third cog 46 assembly for its part has a gear ratio of 16640 micro-steps per turn. The ring for controlling the variable spherical power is adjustable over an angular span of 120° (therefore corresponding to 5547 micro-steps) so as to obtain the variation in spherical power from −25D to 25D (i.e. a span of variation of 50D). The resolution (variation in spherical power $S_V$ for one micro-step) is therefore 0.009 D.

According to one envisionable embodiment, provision may be made for the control element 50 to take into account the distance between the entrance face of the spherical lens 6 and the vertex of the cornea of an eye observing through the visual compensation system, in order optionally to correct the power setpoints of the visual compensation device in question. This distance (sometimes denoted LED for "lens-eye distance") may be obtained by known means for doing so.

Taking the example of a spherical power S of equivalent focal length F, a positioning error $\epsilon$ would mean a corrected focal length F' would be required, equivalent to a spherical power S', where:

$$F' = F - \varepsilon$$

and $$S' = S\left(\frac{1}{1 - \frac{\varepsilon}{F}}\right),$$

which to a first approximation gives $S' = S \cdot (1 + \epsilon \cdot S)$.

The control element 50 therefore determines, according to this embodiment, the values of the angles $\alpha_1$, $\alpha_2$ and the value of spherical power $S_V$ (and the control signals to respectively be applied to the motors as indicated above) not only depending on the setpoint values S, C, $\alpha$ received as input but also depending on the eye-device (here the cornea-entrance face of the lens 6) distance. It will be noted that the lens-eye distance is here taken into account by the control element 50, which receives uncorrected setpoints (i.e. without the lens-eye distance accounted for).

Moreover, provision may be made, during passage from initial setpoint values $\alpha_1$, $\alpha_2$, $S_V$ to new setpoint values $\alpha'_1$, $\alpha'_2$, $S'_V$, for each of the first, second and third motors 42, 44, 46 to be actuated for a given length of time T (in seconds) that may optionally depend on the amplitude of one of the setpoint changes (for example on the variation, in absolute value, in spherical power $|S'_V - S_V|$, where $|x|$ is the absolute value of x).

To do this, the computing machine 66 for example determines the number $p_1$ of micro-steps of the motor 42 allowing passage from the angle $\alpha_1$ to the angle $\alpha'_1$, the number $p_2$ of micro-steps of the motor 44 allowing passage from the angle $\alpha_2$ to the angle $\alpha'_2$ and the number $p_3$ of micro-steps of the motor 46 allowing passage from the spherical power $S_V$ to the spherical power $S'_V$. The computing machine 66 then commands the motor 42 to rotate at a speed of $p_1/T$ micro-steps per second, the motor 44 to rotate at a speed of $p_2/T$ micro-steps per second and the motor 46 to rotate at a speed of $p_3/T$ micro-steps per second.

The control element 50 also comprises a temperature sensor 62, which delivers a datum on measured ambient temperature, and an inclinometer 64, for example taking the form of an accelerometer, which delivers a datum on the orientation of the visual compensation system 10, for example relative to the vertical.

The computing machine 66 receives the temperature datum generated by the temperature sensor 62 and the orientation datum generated by the inclinometer 64 and uses these data in the context of the determination of the commands to send to the motors 42, 44, 46.

In the example described, the control module 70 uses the temperature datum in order to compensate for the variations in spherical power of the lens 6 due to the temperature (about 0.06 D/° C. in the described example) and the orientation datum in order to compensate for possible disturbances of the drive system (motors, worm screws, cogs) due to changes in the orientation of the visual compensation system 10.

The visual compensation system 10 may be used to provide the Jackson-cross-cylinder function, Jackson cross-cylinders also being referred to just as flip cross cylinders.

According to a first example, this function may be used to verify (or even find) an angle $\alpha_0$ of required cylindrical correction (parameter sometimes denoted "cylinder axis"). Here, it is assumed that a spherical power correction value $S_0$ and a cylindrical power correction value $C_0$ have also been determined beforehand.

The Jackson-cross-cylinder function is for example provided by applying in rapid alternation two sets of setpoints, namely a first set of setpoints corresponding to an addition of cylindrical power $C_{var}$ (for example 0.5D) at 45° from the axis defined by the angle $\alpha_0$:
- an angle of astigmatism setpoint $\alpha_1 = \alpha_0 + 0.5 \cdot a\ \tan(C_{var}/C_0)$,
- a cylindrical power setpoint $C_1 = \text{Root}(C_0^2 + C_{var}^2)$, where Root is the square root function; and
- a spherical power setpoint $S_1 = S_0 + C_0/2 - C_1/2$,
and a second set of setpoints corresponding to an addition of cylindrical power $-C_{var}$ at 45° from the axis defined by the angle $\alpha_0$:
- an angle of astigmatism setpoint $\alpha_2 = \alpha_0 - 0.5 \cdot a\ \tan(C_{var}/C_0)$,
- a cylindrical power setpoint $C_2 = \text{Root}(C_p^{2+} C_{var}^2)$, and
- a spherical power setpoint $S_2 = S_0 + C_0/2 - C_2/2$.

According to a second example, this function may be used to verify (or even find) the value of the required cylindrical power correction value $C_0$. Here, it is assumed that a spherical power correction value $S_0$ and an angle of astigmatism value $\alpha_0$ have also been determined beforehand.

The Jackson-cross-cylinder function is for example provided by applying in rapid alternation two sets of setpoints, namely a first set of setpoints corresponding to an addition of cylindrical power $C_{var}$ (for example 0.5D) on the axis defined by the angle $\alpha_0$:
- an angle of astigmatism setpoint $\alpha_1 = \alpha_0$,
- a cylindrical power setpoint $C_1 = C_0 + C_{var}$; and
- a spherical power setpoint $S_1 = S_0 - C_{var}/2$,
and a second set of setpoints corresponding to an addition of cylindrical power $-C_{var}$ on the axis defined by the angle $\alpha_0$:
- an angle of astigmatism setpoint $\alpha_2 = \alpha_0$;
- a cylindrical power setpoint $C_2 = C_0 - C_{var}$; and
- a spherical power setpoint $S_2 = S_0 + C_{var}/2$.

The invention claimed is:

1. A visual compensation system allowing observation along an optical axis of observation with an optical correction of variable power, comprising:
   a first optical element rotatable with a rotary movement centered on the optical axis and having a first cylindrical power along the optical axis;
   a second optical element rotatable with a rotary movement centered on the optical axis and having a second cylindrical power along the optical axis;
   a lens having said optical axis as an axis and being of variable spherical power; and
   a mechanism driven by a motor, the mechanism being configured to drive a ring to rotate in order to control the spherical power of the lens of variable spherical power,
   wherein the lens of variable spherical power is a lens containing a fluid and a deformable membrane.

2. The visual compensation system of claim 1, wherein the first optical element and the second optical element are independently rotatable one from the other so that, in at least one position, the resultant cylindrical power generated by the combination of the first optical element and the second optical element has a value lower than 0.1 diopters.

3. The visual compensation system of claim 1, wherein the first optical element and the second optical element are independently rotatable one from the other so that, in at least one position, the resultant cylindrical power generated by the combination of the first optical element and the second optical element has a value of zero.

4. The visual compensation system of claim 1, wherein the spherical power induced by the combination of the first optical element and the second optical element is at least in part compensated for by the lens of variable spherical power.

5. The visual compensation system of claim 1, wherein a first other mechanism is driven by a first other motor and is configured to rotate the first optical element with a rotary movement centered on the optical axis, and
   a second other mechanism is driven by a second other motor and is configured to rotate the second optical element with a rotary movement centered on the optical axis.

6. The visual compensation system of claim 5, wherein a control element is configured to respectively control the first motor and the second motor depending on setpoint data.

7. The visual compensation system of claim 6, wherein the control element comprises a temperature sensor.

8. The visual compensation system of claim 6, wherein the control element comprises a sensor of orientation or of movement designed to deliver an orientation datum.

9. The visual compensation system of claim 8, wherein the control element comprises a computing machine configured to generate control signals depending on at least one of said setpoint data and said orientation datum and to emit control signals respectively addressed to the first motor and to the second motor.

10. The visual compensation system of claim 6, wherein the control element is configured to generate control signals depending on at least one of said setpoint data and a distance between a portion of the system and an eye observing through the system.

11. The visual compensation system of claim 5, wherein the first other mechanism comprises a first cog that interacts with a first worm screw that is securely fastened to a driveshaft of the first other motor, the first optical element being mounted on the first cog, and
   wherein the second other mechanism comprises a second cog that interacts with a second worm screw that is securely fastened to a driveshaft of the second other motor, the second optical element being mounted on the second cog.

12. The visual compensation system of claim 1, wherein a first other mechanism is driven by a first other motor and is configured to rotate the first optical element with a rotary movement centered on the optical axis,
   a second other mechanism is driven by a second other motor and is configured to rotate the second optical element with a rotary movement centered on the optical axis, and
   said mechanism configured to drive the ring to rotate comprises a third cog that interacts with a third worm screw that is securely fastened to a driveshaft of said motor, the controlling ring being securely fastened to the third cog.

13. The visual compensation system of claim 12, wherein the first other mechanism comprises a first cog that interacts with a first worm screw that is securely fastened to a driveshaft of the first other motor, the first optical element being mounted on the first cog,
   the second other mechanism comprises a second cog that interacts with a second worm screw that is securely fastened to a driveshaft of the second other motor, the second optical element being mounted on the second cog, and
   the first other motor, the second other motor and said motor are disposed to free a circular geometry over at least 120°, said geometry being centered on the optical axis at a distance smaller than 20 mm from the effective radius of the lenses.

14. The visual compensation system of claim 11, further comprising at least one optical cell associated with one of said cogs so as to determine the position of the associated optical element.

15. The visual compensation system of claim 1, wherein the first optical element, the second optical element, and the lens are mounted to preserve their respective setpoint positions without a supply of electrical power.

16. The visual compensation system of claim 1, wherein the first optical element and the second optical element are separated by a space of dimension smaller than 1 mm along the optical axis.

17. The visual compensation system of claim 1, wherein the first optical element is a first diopter formed on a face of a first planar-cylindrical lens, and
   the second optical element is a second diopter formed on a face of a second planar-cylindrical lens.

18. The visual compensation system of claim 17, wherein the first optical element is a convex planar-cylindrical lens, and
   the second optical element is a concave planar-cylindrical lens.

19. The visual compensation system of claim 1, wherein the first optical element, the second optical element, and the lens are controlled to provide a Jackson-cross-cylinder function.

20. A visual compensation system allowing observation along an optical axis of observation with an optical correction of variable power, further comprising:
   a first optical element rotatable with a rotary movement centered on the optical axis and having a first cylindrical power along the optical axis;

a second optical element rotatable with a rotary movement centered on the optical axis and having a second cylindrical power along the optical axis;

a lens having said optical axis as an axis, the lens being of variable spherical power and mechanically actuatable to make said spherical power vary continuously; and a mechanism driven by a motor, the mechanism being configured to drive a ring to rotate in order to control the spherical power of the lens of variable spherical power, wherein the lens of variable spherical power is a lens containing a fluid and a deformable membrane.

21. An optometric binocular device comprising:

two optical systems, at least one of the two optical systems being the visual compensation system according to claim 1.

22. An optometric binocular device comprising:

two optical systems, at least one of the two optical systems being the visual compensation system according to claim 20.

23. The visual compensation system of claim 1, wherein the ring is mounted on a casing and the rotation of the ring translates a part of the lens of variable spherical power, thereby causing deformation of the membrane, the membrane being transparent.

* * * * *